United States Patent [19]
Vogelstein

[11] Patent Number: 5,874,545
[45] Date of Patent: Feb. 23, 1999

[54] DCC ANTIBODIES

[75] Inventor: Bert Vogelstein, Baltimore, Md.

[73] Assignee: The Johns Hopkins University, Baltimore, Md.

[21] Appl. No.: 442,977

[22] Filed: May 17, 1995

Related U.S. Application Data

[62] Division of Ser. No. 227,527, Apr. 14, 1994, Pat. No. 5,532,108, which is a continuation of Ser. No. 460,981, Jan. 4, 1990, abandoned.

[51] Int. Cl.$^6$ .......................... C07K 16/30; C07K 16/00; C07K 16/18
[52] U.S. Cl. ................................. 530/388.85; 530/388.8; 530/388.1; 530/389.1; 530/389.9; 436/64
[58] Field of Search ........................... 530/388.8, 388.85, 530/388.1, 389.1, 389.9; 436/64, 813; 435/7.23

[56] References Cited

U.S. PATENT DOCUMENTS 4,831,124  5/1989  Paddock ..................................... 536/27

OTHER PUBLICATIONS

Sevier, E.D. et al, Clin Chem, 27(11):1797–1806, 1981.
Maurer, P.H et al, Meth in Enzym, 70:49–70, 1980.
Vogelstein et al., *N. Eng. J. Med.* (1988), 319:525–532.
Kern et al., *JAMA* (1989), 261:3099–3103.
Baker et al., *Science* (1989), 244:217–221.
Sanger et al., *Proc. Natl. Acad. Sci. USA* (1977), 74(2):5463–5467.
Frati et al., "Genetics and Phenotypic Markers of Tumors," Aaronson, ed., Plenum Press, pp. 1–20, 1984.
Friedmann et al, *Science* (1989), 244:1275–1281.
Engelke et al., *Proc. Natl. Acad. Sci. USA* (1988), 85:544–548.
Old et al., Principles of Gene Manipulation, 3rd Edition, Blackwell Scientific Public.

Fearon et al., "Identification of a Chromosome 18q Gene that is Altered in Colorectal Cancers," *Science* (1990), 247:49–56.
Kern et al., "Clinical and Pathological Associations with Allelic Loss in Colorectal Carcinoma," *JAMA* (1989), 261:3099–3103.
Vogelstein et al., "Genetic Alterations During Colorectal–Tumor Development," *N. Eng. J. Med.* (1988), 319:525–532.
Marlhens et al., "RFLP Identified by the Anonymous DNA Segment OL VII E10 at 18q21.3 (HGM No. D18S8)," *Nucleic Acids Res.* (1987), 15:1348.
Lynch et al., Hereditary Nonpolyposis Colorectal Cancer (Lynch Syndromes I and II), *Cancer* (1985), 56:934–938.
O'Connell et al., "Twelve Loci Form a Continuous Linkage Map for Human Chromosome 18," *Genomics* (1988), 3;367–372.
Geitvik et al., "The Kidd (JK) Blood Group Locus Assigned to Chromosome 18 by Close Linkage to a DNA–RFLP," *Hum. Genet.* (1987), 77:205–209.
Stanley et al., "Construction of a New Family of High Efficiency Bacterial Expression Vectors: Identificatio of cDNA Clones Coding for Human Liver Proteins," *EMBO Journal* (1984), 3:1429–1434.
Maxam et al., "A New Method for Sequencing DNA", *Proc. Natl. Acad. Sci.*, 74(2):560–564 (1977).
Boman et al., *Biochem. Biophys. Res. Commun.* 155(1):463–469 (1988).
Bishop et al., "The Genetics of Colorectal Cancer", *Cancer Surveys* 9(4):586–604 (1990).

*Primary Examiner*—Susan A. Loring
*Attorney, Agent, or Firm*—Banner & Witcoff, Ltd.

[57] ABSTRACT

A new human gene termed DCC is disclosed. Methods and kits are provided for assessing mutations of the DCC gene in human tissues and body samples. Insertion, deletion, and point mutations in DCC are observed in human tumor cells. Normal tissues express DCC while most colorectal cancers do not. Loss of wild-type DCC genes is associated with neoplastic progression and a diminished life expectancy.

6 Claims, 20 Drawing Sheets

FIG. 2
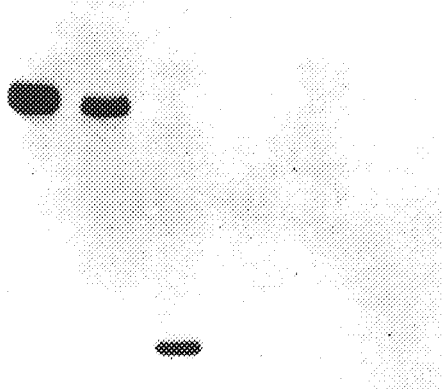
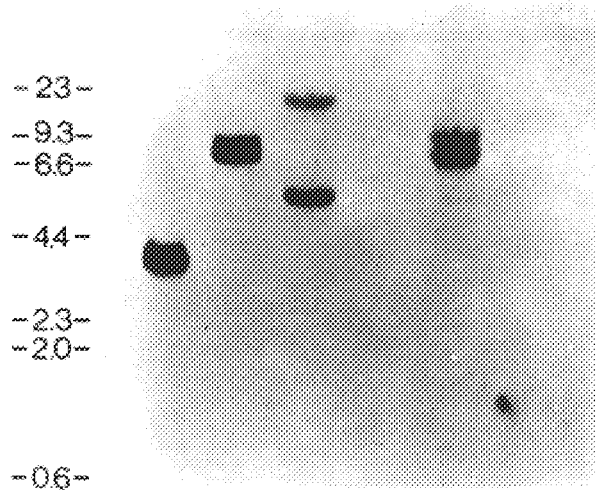

FIG. 3A

FRAGMENT G

```
HUMAN   ATTTGGAAGACTTATTCTTCCTTCTTTG
RAT     T  GAAAT  CT A CC T CT G TG CT
AA
```

```
HUMAN   TTC ATG GGA GAC ACA GTG CTA
RAT             T           T
AA       F   M   G   D   T   V   L
```

```
HUMAN   AAC CAA CAA GAC CTG ACT CCA
RAT      T           C   C
AA       N   Q   Q   D   L   T   P
```

FRAGMENT O

```
HUMAN   CTCACTCACTTTTTTTTTCTGTCTTTG
RAT            T  C  G
AA
```

```
HUMAN   ATG GAT ATT GAG TTT GAA TGT
RAT          C
AA       M   D   I   E   F   E   C
```

```
HUMAN   GTC ATT CCT AGT GAT TAT TTT
RAT      G  --- --- --- --- --- ---
AA       V   I   P   S   D   Y   F
```

FRAGMENT P

```
HUMAN   TACTTTACCTGCTTTTTCTTTTCCCTAG
RAT     ----------------------------
AA
```

```
HUMAN   TAT CAA TGT GTG GCT GAA AAT
RAT
AA       Y   Q   C   V   A   E   N
```

FIG. 3B

```
        ▼
TTTTTCTCCTAG GA CCA CTG AGG TTC CTT TCA
   C C    T                      C   C
              P   L   R   F   L   S

CTC AAG TGT GAA GTC ATT GGG GAG CCC ATG
 T                            C
 L   K   C   E   V   I   G  E/D  P   M

ATC CCA GGT GAC TCC CGA GTG GTG GTC
 AC      G   A       G   T       C
I/N  P   G   D   S   R   V   V   V

▼
CAG TT CCG CCA TGG TTT TTA AAT CAT CCT
                                 C
         P   P   W   F   L   N   H   P

ACA GTC TCT GGA AAG CCT GTG CCC ACT GTG
 G       G   C   G
T/A  V   S   G   K   P   V   P   T   V

▼
CAG ATA GTG GTAATT
--- --- ---
 Q   I   V

GGA GGA AGC AAC TTA CGG ATA CTT GGG GTG
--- --- --- --- --- --       C
 G   G   S   N   L   R   I   L   G   V

GAG GCT GGA AAT GCC CAG ACC AGT GCA CAG
         C           A   GT      C
 E   A   G   N   A   Q  T/S  S   A   Q
```

FIG. 3C

```
CAG ACA GAA TCT GTC ACA GCC
                 A
 Q   T   E   S   I   T   A

CCA ACA ATC CAC TGG CAG AAG
             A
 P   T   I   H   W   Q   K

TCC AAC CTG TAT GCC TAT GAA AGC
             C
 S   N   L   Y   A   Y   E   S

AAT TGG ATG AAG AAT GGA GAT GTG

N   W   M   K   N   G   D   V

GTG AAG TCA GAT GAA GGC TTT
         A
 V   K   S   D   E   G   F
                         ▼
CTC ATT GTC CCT AAG CCT GGTAAGACAAT
 G           C       C       C
 L   I   V   P   K   P
```

Figure 4A

| | |
|---|---|
| C CAA CTC CCA GCT CGC ACA CCG CTG GCG ACA CCC CAG TAA CAA GTG<br>  Gln Leu Pro Ala Arg Thr Pro Leu Ala Thr Pro Gln  \*  Gln Val<br>   1              5                     10                   15 | 46 |
| AGA GCG CTC CAC CCC GCA GTC CCC CCC GCC TCT CCT CCC TGG GTC CCC<br>Arg Ala Leu His Pro Ala Val Pro Pro Ala Ser Pro Pro Trp Val Pro<br>               20                  25               30 | 94 |
| TCG GCT CTC GGA AGA AAA ACC AAC AGC ATC TCC AGC TCT CGC GCG GAA<br>Ser Ala Leu Gly Arg Lys Thr Asn Ser Ile Ser Ser Ser Arg Ala Glu<br>               35                  40               45 | 142 |
| TTG TCT CTT CAA CTT TAC CCA ACC GAC GAC AAG GAA CCA GCC TCA ACC<br>Leu Ser Leu Gln Leu Tyr Pro Thr Asp Asp Lys Glu Pro Ala Ser Thr<br>        50                     55                 60 | 190 |
| TTT TAA TGC ACA GCC CGG CCA CAG GAT TGC CTT CCA TCT CCT CTT GGT<br>Phe  \*  Cys Thr Ala Arg Pro Gln Asp Cys Leu Pro Ser Pro Leu Gly<br>    65                     70                  75 | 238 |
| CCC TCC TGG ATG TGG TTT ATT GAT GAC TTG CGA GCC CCT CAG AGA GCT<br>Pro Ser Trp Met Trp Phe Ile Asp Asp Leu Arg Ala Pro Gln Arg Ala<br>80                  85                  90               95 | 286 |
| GTC TTC CCT CCT CTG GCT CCC TCC GTT TCC TTG AGT TAG TTT TCT AAG<br>Val Phe Pro Pro Leu Ala Pro Ser Val Ser Leu Ser  \*  Phe Ser Lys<br>              100                105             110 | 334 |
| GTT TTA CCG GGG CTC GGG ATC TCT TGG ACC GAA TGG AAC TTT TTG CTG<br>Val Leu Pro Gly Leu Gly Ile Ser Trp Thr Glu Trp Asn Phe Leu Leu<br>             115                120             125 | 382 |
| CCT GCT TTT GCT GCT GAT TCT GTC AGT GGA CAA GGA AAA AGG CTT CGA<br>Pro Ala Phe Ala Ala Asp Ser Val Ser Gly Gln Gly Lys Arg Leu Arg<br>        130                  135             140 | 430 |
| AGG CAG CAG AGG CGC AGG GGA GGT GGA GAA AGA GGT GGA GGA AGA GGA<br>Arg Gln Gln Arg Arg Arg Gly Gly Gly Glu Arg Gly Gly Gly Arg Gly<br>    145                     150             155 | 478 |
| CGA GGA GGA GGA GGA AGC CGA AGG GGC TCG GCG CGT GTG TGT GCA TGT<br>Arg Gly Gly Gly Gly Ser Arg Arg Gly Ser Ala Arg Val Cys Ala Cys<br>160                 165                170             175 | 526 |
| GTG CAT GCG TGT GTG AGT GCA TGT GTG TGA GTG CTG CCG CTG CCC GCG<br>Val His Ala Cys Val Ser Ala Cys Val  \*  Val Leu Pro Leu Pro Ala<br>          180                  185             190 | 574 |
| ACC CCT GGC CCC GAA GGT GTT GGC TGA AAT ATG GAG AAT AGT CTT AGA<br>Thr Pro Gly Pro Glu Gly Val Gly  \*  Asn Met Glu Asn Ser Leu Arg<br>             195                200             205 | 622 |
| TGT GTT TGG GTA CCC AAG CTG GCT TTT GTA CTC TTC GGA GCT TCC TTG<br>Cys Val Trp Val Pro Lys Leu Ala Phe Val Leu Phe Gly Ala Ser Leu<br>        210                  215             220 | 670 |

Figure 4B

```
CTC AGC GCG CAT CTT CAA GTA ACC GGT TTT CAA ATT AAA GCT TTC ACA        718
Leu Ser Ala His Leu Gln Val Thr Gly Phe Gln Ile Lys Ala Phe Thr
    225             230                 235

GCA CTG CGC TTC CTC TCA GAA CCT TCT GAT GCC GTC ACA ATG CGG GGA        766
Ala Leu Arg Phe Leu Ser Glu Pro Ser Asp Ala Val Thr Met Arg Gly
240             245                 250                 255

GGA AAT GTC CTC CTC GAC TGC TCC GCG GAG TCC GAC CGA GGA GTT CCA        814
Gly Asn Val Leu Leu Asp Cys Ser Ala Glu Ser Asp Arg Gly Val Pro
                260                 265                 270

GTG ATC AAG TGG AAG AAA GAT GGC ATT CAT CTG GCC TTG GGA ATG GAT        862
Val Ile Lys Trp Lys Lys Asp Gly Ile His Leu Ala Leu Gly Met Asp
            275                 280                 285

GAA AGG AAG CAG CAA CTT TCA AAT GGG TCT CTG CTG ATA CAA AAC ATA        910
Glu Arg Lys Gln Gln Leu Ser Asn Gly Ser Leu Leu Ile Gln Asn Ile
        290                 295                 300

CTT CAT TCC AGA CAC CAC AAG CCA GAT GAG GGA CTT TAC CAA TGT GAG        958
Leu His Ser Arg His His Lys Pro Asp Glu Gly Leu Tyr Gln Cys Glu
    305                 310                 315

GCA TCT TTA GGA GAT TCT GGC TCA ATT ATT AGT CGG ACA GCA AAA GTT       1006
Ala Ser Leu Gly Asp Ser Gly Ser Ile Ile Ser Arg Thr Ala Lys Val
320             325                 330                 335

GCA GTA GCA GGA CCA CTG AGG TTC CTT TCA CAG ACA GAA TCT GTC ACA       1054
Ala Val Ala Gly Pro Leu Arg Phe Leu Ser Gln Thr Glu Ser Val Thr
                340                 345                 350

GCC TTC ATG GGA GAC ACA GTG CTA CTC AAG TGT GAA GTC ATT GGG GAG       1102
Ala Phe Met Gly Asp Thr Val Leu Leu Lys Cys Glu Val Ile Gly Glu
            355                 360                 365

CCC ATG CCA ACA ATC CAC TGG CAG AAG AAC CAA CAA GAC CTG ACT CCA       1150
Pro Met Pro Thr Ile His Trp Gln Lys Asn Gln Gln Asp Leu Thr Pro
        370                 375                 380

ATC CCA GGT GAC TCC CGA GTG GTG GTC TTG CCC TCT GGA GCA TTG CAG       1198
Ile Pro Gly Asp Ser Arg Val Val Val Leu Pro Ser Gly Ala Leu Gln
    385                 390                 395

ATC AGC CGA CTC CAA CCG GGG GAC ATT GGA ATT TAC CGA TGC TCA GCT       1246
Ile Ser Arg Leu Gln Pro Gly Asp Ile Gly Ile Tyr Arg Cys Ser Ala
400             405                 410                 415

CGA AAT CCA GCC AGC TCA AGA ACA GGA AAT GAA GCA GAA GTC AGA ATT       1294
Arg Asn Pro Ala Ser Ser Arg Thr Gly Asn Glu Ala Glu Val Arg Ile
                420                 425                 430

TTA TCA GAT CCA GGA CTG CAT AGA CAG CTG TAT TTT CTG CAA AGA CCA       1342
Leu Ser Asp Pro Gly Leu His Arg Gln Leu Tyr Phe Leu Gln Arg Pro
            435                 440                 445
```

Figure 4C

| | |
|---|---|
| TCC AAT GTA GTA GCC ATT GAA GGA AAA GAT GCT GTC CTG GAA TGT TGT<br>Ser Asn Val Val Ala Ile Glu Gly Lys Asp Ala Val Leu Glu Cys Cys<br>     450                 455               460 | 1390 |
| GTT TCT GGC TAT CCT CCA CCA AGT TTT ACC TGG TTA CGA GGC GAG GAA<br>Val Ser Gly Tyr Pro Pro Pro Ser Phe Thr Trp Leu Arg Gly Glu Glu<br>    465                470               475 | 1438 |
| GTC ATC CAA CTC AGG TCT AAA AAG TAT TCT TTA TTG GGT GGA AGC AAC<br>Val Ile Gln Leu Arg Ser Lys Lys Tyr Ser Leu Leu Gly Gly Ser Asn<br>480                 485              490               495 | 1486 |
| TTG CTT ATC TCC AAT GTG ACA GAT GAT GAC AGT GGA ATG TAT ACC TGT<br>Leu Leu Ile Ser Asn Val Thr Asp Asp Asp Ser Gly Met Tyr Thr Cys<br>             500               505              510 | 1534 |
| GTT GTC ACA TAT AAA AAT GAG AAT ATT AGT GCC TCT GCA GAG CTC ACA<br>Val Val Thr Tyr Lys Asn Glu Asn Ile Ser Ala Ser Ala Glu Leu Thr<br>        515               520              525 | 1582 |
| GTC TTG GTT CCG CCA TGG TTT TTA AAT CAT CCT TCC AAC CTG TAT GCC<br>Val Leu Val Pro Pro Trp Phe Leu Asn His Pro Ser Asn Leu Tyr Ala<br>        530               535              540 | 1630 |
| TAT GAA AGC ATG GAT ATT GAG TTT GAA TGT ACA GTC TCT GGA AAG CCT<br>Tyr Glu Ser Met Asp Ile Glu Phe Glu Cys Thr Val Ser Gly Lys Pro<br>    545                550              555 | 1678 |
| GTG CCC ACT GTG AAT TGG ATG AAG AAT GGA GAT GTG GTC ATT CCT AGT<br>Val Pro Thr Val Asn Trp Met Lys Asn Gly Asp Val Val Ile Pro Ser<br>560                 565              570              575 | 1726 |
| GAT TAT TTT CAG ATA GTG GGA GGA AGC AAC TTA CGG ATA CTT GGG GTG<br>Asp Tyr Phe Gln Ile Val Gly Gly Ser Asn Leu Arg Ile Leu Gly Val<br>             580                585             590 | 1774 |
| GTG AAG TCA GAT GAA GGC TTT TAT CAA TGT GTG GCT GAA AAT GAG GCT<br>Val Lys Ser Asp Glu Gly Phe Tyr Gln Cys Val Ala Glu Asn Glu Ala<br>        595             600              605 | 1822 |
| GGA AAT GCC CAG ACC AGT GCA CAG CTC ATT GTC CCT AAG CCT GCA ATC<br>Gly Asn Ala Gln Thr Ser Ala Gln Leu Ile Val Pro Lys Pro Ala Ile<br>        610               615              620 | 1870 |
| CCA AGC TCC AGT GTC CTC CCT TCG GCT CCC AGA GAT GTG GTC CCT GTC<br>Pro Ser Ser Ser Val Leu Pro Ser Ala Pro Arg Asp Val Val Pro Val<br>    625                630              635 | 1918 |
| TTG GTT TCC AGC CGA TTT GTC CGT CTC AGC TGG CGC CCA CCT GCA GAA<br>Leu Val Ser Ser Arg Phe Val Arg Leu Ser Trp Arg Pro Pro Ala Glu<br>640                 645              650              655 | 1966 |
| GCG AAA GGG AAC ATT CAA ACT TTC ACG GTC TTT TTC TCC AGA GAA GGT<br>Ala Lys Gly Asn Ile Gln Thr Phe Thr Val Phe Phe Ser Arg Glu Gly<br>             660                665             670 | 2014 |
| GAC AAC AGG GAA CGA GCA TTG AAT ACA ACA CAG CCT GGG TCC CTT CAG<br>Asp Asn Arg Glu Arg Ala Leu Asn Thr Thr Gln Pro Gly Ser Leu Gln<br>        675             680              685 | 2062 |

Figure 4D

| | |
|---|---|
| CTC ACT GTG GGA AAC CTG AAG CCA GAA GCC ATG TAC ACC TTT CGA GTT<br>Leu Thr Val Gly Asn Leu Lys Pro Glu Ala Met Tyr Thr Phe Arg Val<br>     690                     695                  700 | 2110 |
| GTG GCT TAC AAT GAA TGG GGA CCG GGA GAG AGT TCT CAA CCC ATC AAG<br>Val Ala Tyr Asn Glu Trp Gly Pro Gly Glu Ser Ser Gln Pro Ile Lys<br>     705                     710                  715 | 2158 |
| GTG GCC ACA CAG CCT GAG TTG CAA GTT CCA GGG CCA GTA GAA AAC CTG<br>Val Ala Thr Gln Pro Glu Leu Gln Val Pro Gly Pro Val Glu Asn Leu<br>720                  725                  730               735 | 2206 |
| CAA GCT GTA TCT ACC TCA CCT ACC TCA ATT CTT ATT ACC TGG GAA CCC<br>Gln Ala Val Ser Thr Ser Pro Thr Ser Ile Leu Ile Thr Trp Glu Pro<br>               740                  745                750 | 2254 |
| CCT GCC TAT GCA AAC GGT CCA GTC CAA GGT TAC AGA TTG TTC TGC ACT<br>Pro Ala Tyr Ala Asn Gly Pro Val Gln Gly Tyr Arg Leu Phe Cys Thr<br>          755                     760                765 | 2302 |
| GAG GTG TCC ACA GGA AAA GAA CAG AAT ATA GAG GTT GAT GGA CTA TCT<br>Glu Val Ser Thr Gly Lys Glu Gln Asn Ile Glu Val Asp Gly Leu Ser<br>          770                     775                780 | 2350 |
| TAT AAA CTG GAA GGC CTG AAA AAA TTC ACC GAA TAT AGT CTT CGA TTC<br>Tyr Lys Leu Glu Gly Leu Lys Lys Phe Thr Glu Tyr Ser Leu Arg Phe<br>     785                     790                  795 | 2398 |
| TTA GCT TAT AAT CGC TAT GGT CCG GGC GTC TCT ACT GAT GAT ATA ACA<br>Leu Ala Tyr Asn Arg Tyr Gly Pro Gly Val Ser Thr Asp Asp Ile Thr<br>800                  805                  810               815 | 2446 |
| GTG GTT ACA CTT TCT GAC GTG CCA AGT GCC CCG CCT CAG AAC GTC TCC<br>Val Val Thr Leu Ser Asp Val Pro Ser Ala Pro Pro Gln Asn Val Ser<br>               820                  825                830 | 2494 |
| CTG GAA GTG GTC AAT TCA AGA AGT ATC AAA GTT AGC TGG CTG CCT CCT<br>Leu Glu Val Val Asn Ser Arg Ser Ile Lys Val Ser Trp Leu Pro Pro<br>          835                     840                845 | 2542 |
| CCA TCA GGA ACA CAA AAT GGA TTT ATT ACC GGC TAT AAA ATT CGA CAC<br>Pro Ser Gly Thr Gln Asn Gly Phe Ile Thr Gly Tyr Lys Ile Arg His<br>     850                     855                  860 | 2590 |
| AGA AAG ACG ACC CGC AGG GGT GAG ATG GAA ACA CTG GAG CCA AAC AAC<br>Arg Lys Thr Thr Arg Arg Gly Glu Met Glu Thr Leu Glu Pro Asn Asn<br>     865                     870                875 | 2638 |
| CTC TGG TAC CTA TTC ACA GGA CTG GAG AAA GGA AGT CAG TAC AGT TTC<br>Leu Trp Tyr Leu Phe Thr Gly Leu Glu Lys Gly Ser Gln Tyr Ser Phe<br>880                  885                  890               895 | 2686 |
| CAG GTG TCA GCC ATG ACA GTC AAT GGT ACT GGA CCA CCT TCC AAC TGG<br>Gln Val Ser Ala Met Thr Val Asn Gly Thr Gly Pro Pro Ser Asn Trp<br>               900                  905                910 | 2734 |

Figure 4E

```
TAT ACT GCA GAG ACT CCA GAG AAT GAT CTA GAT GAA TCT CAA GTT CCT      2782
Tyr Thr Ala Glu Thr Pro Glu Asn Asp Leu Asp Glu Ser Gln Val Pro
            915                 920                 925

GAT CAA CCA AGC TCT CTT CAT GTG AGG CCC CAG ACT AAC TGC ATC ATC      2830
Asp Gln Pro Ser Ser Leu His Val Arg Pro Gln Thr Asn Cys Ile Ile
            930                 935                 940

ATG AGT TGG ACT CCT CCC TTG AAC CCA AAC ATC GTG GTG CGA GGT TAT      2878
Met Ser Trp Thr Pro Pro Leu Asn Pro Asn Ile Val Val Arg Gly Tyr
            945                 950                 955

ATT ATC GGT TAT GGC GTT GGG AGC CCT TAC GCT GAG ACA GTG CGT GTG      2926
Ile Ile Gly Tyr Gly Val Gly Ser Pro Tyr Ala Glu Thr Val Arg Val
960                 965                 970                 975

GAC AGC AAG CAG CGA TAT TAT TCC ATT GAG AGG TTA GAG TCA AGT TCC      2974
Asp Ser Lys Gln Arg Tyr Tyr Ser Ile Glu Arg Leu Glu Ser Ser Ser
            980                 985                 990

CAT TAT GTA ATC TCC CTA AAA GCT TTT AAC AAT GCC GGA GAA GGA GTT      3022
His Tyr Val Ile Ser Leu Lys Ala Phe Asn Asn Ala Gly Glu Gly Val
            995                 1000                1005

CCT CTT TAT GAA AGT GCC ACC ACC AGG TCT ATA ACC GAT CCC ACT GAC      3070
Pro Leu Tyr Glu Ser Ala Thr Thr Arg Ser Ile Thr Asp Pro Thr Asp
            1010                1015                1020

CCA GTT GAT TAT TAT CCT TTG CTT GAT GAT TTC CCC ACC TCG GTC CCA      3118
Pro Val Asp Tyr Tyr Pro Leu Leu Asp Asp Phe Pro Thr Ser Val Pro
            1025                1030                1035

GAT CTC TCC ACC CCC ATG CTC CCA CCA GTA GGT GTA CAG GCT GTG GCT      3166
Asp Leu Ser Thr Pro Met Leu Pro Pro Val Gly Val Gln Ala Val Ala
1040                1045                1050                1055

CTT ACC CAT GAT GCT GTG AGG GTC AGC TGG GCA GAC AAC TCT GTC CCT      3214
Leu Thr His Asp Ala Val Arg Val Ser Trp Ala Asp Asn Ser Val Pro
            1060                1065                1070

AAG AAC CAA AAG ACG TCT GAG GTG CGA CTT TAC ACC GTC CGG TGG AGA      3262
Lys Asn Gln Lys Thr Ser Glu Val Arg Leu Tyr Thr Val Arg Trp Arg
            1075                1080                1085

ACC AGC TTT TCT GCA AGT GCA AAA TAC AAG TCA GAA GAC ACA ACA TCT      3310
Thr Ser Phe Ser Ala Ser Ala Lys Tyr Lys Ser Glu Asp Thr Thr Ser
            1090                1095                1100

CTA AGT TAC ACA GCA ACA GGC CTC AAA CCA AAC ACA ATG TAT GAA TTC      3358
Leu Ser Tyr Thr Ala Thr Gly Leu Lys Pro Asn Thr Met Tyr Glu Phe
            1105                1110                1115

TCG GTC ATG GTA ACA AAA AAC AGA AGG TCC AGT ACT TGG AGC ATG ACT      3406
Ser Val Met Val Thr Lys Asn Arg Arg Ser Ser Thr Trp Ser Met Thr
1120                1125                1130                1135
```

Figure 4F

| | |
|---|---|
| GCA CAT GCC ACC ACG TAT GAA GCA GCC CCC ACC TCT GCT CCC AAG GAC<br>Ala His Ala Thr Thr Tyr Glu Ala Ala Pro Thr Ser Ala Pro Lys Asp<br>               1140                      1145                   1150 | 3454 |
| TTT ACA GTC ATT ACT AGG GAA GGG AAG CCT CGT GCC GTC ATT GTG AGT<br>Phe Thr Val Ile Thr Arg Glu Gly Lys Pro Arg Ala Val Ile Val Ser<br>           1155                   1160                   1165 | 3502 |
| TGG CAG CCT CCC TTG GAA GCC AAT GGG AAA ATT ACT GCT TAC ATC TTA<br>Trp Gln Pro Pro Leu Glu Ala Asn Gly Lys Ile Thr Ala Tyr Ile Leu<br>          1170                   1175                  1180 | 3550 |
| TTT TAT ACC TTG GAC AAG AAC ATC CCA ATT GAT GAC TGG ATT ATG GAA<br>Phe Tyr Thr Leu Asp Lys Asn Ile Pro Ile Asp Asp Trp Ile Met Glu<br>      1185                  1190                  1195 | 3598 |
| ACA ATC AGT GGT GAT AGG CTT ACT CAT CAA ATC ATG GAT CTC AAC CTT<br>Thr Ile Ser Gly Asp Arg Leu Thr His Gln Ile Met Asp Leu Asn Leu<br>1200                  1205                  1210                 1215 | 3646 |
| GAT ACT ATG TAT TAC TTT CGA ATT CAA GCA CGA AAT TCA AAA GGA GTG<br>Asp Thr Met Tyr Tyr Phe Arg Ile Gln Ala Arg Asn Ser Lys Gly Val<br>          1220                   1225                  1230 | 3694 |
| GGG CCA CTC TCT GAT CCC ATC CTC TTC AGG ACT CTG AAA GTG GAA CAC<br>Gly Pro Leu Ser Asp Pro Ile Leu Phe Arg Thr Leu Lys Val Glu His<br>             1235                  1240                  1245 | 3742 |
| CCT GAC AAA ATG GCT AAT GAC CAA GGT CGT CAT GGA GAT GGA GGT TAT<br>Pro Asp Lys Met Ala Asn Asp Gln Gly Arg His Gly Asp Gly Gly Tyr<br>         1250                   1255                  1260 | 3790 |
| TGG CCA GTT GAT ACT AAT TTG ATT GAT AGA AGC ACC CTA AAT GAG CCG<br>Trp Pro Val Asp Thr Asn Leu Ile Asp Arg Ser Thr Leu Asn Glu Pro<br>      1265                  1270                  1275 | 3838 |
| CCA ATT GGA CAA ATG CAC CCC CCG CAT GGC AGT GTC ACT CCT CAG AAG<br>Pro Ile Gly Gln Met His Pro Pro His Gly Ser Val Thr Pro Gln Lys<br>1280                  1285                  1290                 1295 | 3886 |
| AAC AGC AAC CTG CTT GTG ATC ATT GTG GTC ACC GTT GGT GTC ATC ACA<br>Asn Ser Asn Leu Leu Val Ile Ile Val Val Thr Val Gly Val Ile Thr<br>            1300                  1305                  1310 | 3934 |
| GTG CTG GTA GTG GTC ATC GTG GCT GTG ATT TGC ACC CGA CGC TCT TCA<br>Val Leu Val Val Val Ile Val Ala Val Ile Cys Thr Arg Arg Ser Ser<br>         1315                   1320                  1325 | 3982 |
| GCC CAG CAG AGA AAG AAA CGG GCC ACC CAC AGT GCT GGC AAA AGG AAG<br>Ala Gln Gln Arg Lys Lys Arg Ala Thr His Ser Ala Gly Lys Arg Lys<br>            1330                  1335                  1340 | 4030 |
| GGC AGC CAG AAG GAC CTC CGA CCC CCT GAT CTT TGG ATC CAT CAT GAA<br>Gly Ser Gln Lys Asp Leu Arg Pro Pro Asp Leu Trp Ile His His Glu<br>         1345                   1350                  1355 | 4078 |

Figure 4G

| | |
|---|---|
| GAA ATG GAG ATG AAA AAT ATT GAA AAG CCA TCT GGC ACT GAC CCT GCA<br>Glu Met Glu Met Lys Asn Ile Glu Lys Pro Ser Gly Thr Asp Pro Ala<br>1360                    1365                   1370                   1375 | 4126 |
| GGA AGG GAC TCT CCC ATC CAA AGT TGC CAA GAC CTC ACA CCA GTC AGC<br>Gly Arg Asp Ser Pro Ile Gln Ser Cys Gln Asp Leu Thr Pro Val Ser<br>                  1380                   1385                   1390 | 4174 |
| CAC AGC CAG TCA GAA ACC CAA CTG GGA AGC AAA AGC ACC TCT CAT TCA<br>His Ser Gln Ser Glu Thr Gln Leu Gly Ser Lys Ser Thr Ser His Ser<br>                 1395                   1400                   1405 | 4222 |
| GGT CAA GAC ACT GAG GAA GCA GGG AGC TCT ATG TCC ACT CTG GAG AGG<br>Gly Gln Asp Thr Glu Glu Ala Gly Ser Ser Met Ser Thr Leu Glu Arg<br>           1410                   1415                   1420 | 4270 |
| TCG CTG GCT GCA CGC CGA GCC CCC CGG GCC AAG CTC ATG ATT CCC ATG<br>Ser Leu Ala Ala Arg Arg Ala Pro Arg Ala Lys Leu Met Ile Pro Met<br>           1425                   1430                   1435 | 4318 |
| GAT GCC CAG TCC AAC AAT CCT GCT GTC GTG AGC GCC ATC CCG GTG CCA<br>Asp Ala Gln Ser Asn Asn Pro Ala Val Val Ser Ala Ile Pro Val Pro<br>1440                    1445                   1450                   1455 | 4366 |
| ACG CTA GAA AGT GCC CAG TAC CCA GGA ATC CTC CCG TCT CCC ACC TGT<br>Thr Leu Glu Ser Ala Gln Tyr Pro Gly Ile Leu Pro Ser Pro Thr Cys<br>                 1460                   1465                   1470 | 4414 |
| GGA TAT CCC CAC CCG CAG TTC ACT CTC CGG CCT GTG CCA TTC CCA ACA<br>Gly Tyr Pro His Pro Gln Phe Thr Leu Arg Pro Val Pro Phe Pro Thr<br>                 1475                   1480                   1485 | 4462 |
| CTC TCA GTG GAC CGA GGT TTC GGA GCA GGA AGA AGT CAG TCA GTG AGT<br>Leu Ser Val Asp Arg Gly Phe Gly Ala Gly Arg Ser Gln Ser Val Ser<br>           1490                   1495                   1500 | 4510 |
| GAA GGA CCA ACT ACC CAA CAA CCA CCT ATG CTG CCC CCA TCT CAG CCT<br>Glu Gly Pro Thr Thr Gln Gln Pro Pro Met Leu Pro Pro Ser Gln Pro<br>           1505                   1510                   1515 | 4558 |
| GAG CAT TCT AGC AGC GAG GAG GCA CCA AGC AGA ACC ATC CCC ACA GCT<br>Glu His Ser Ser Ser Glu Glu Ala Pro Ser Arg Thr Ile Pro Thr Ala<br>1520                    1525                   1530                   1535 | 4606 |
| TGT GTT CGA CCA ACT CAC CCA CTC CGC AGC TTT GCT AAT CCT TTG CTA<br>Cys Val Arg Pro Thr His Pro Leu Arg Ser Phe Ala Asn Pro Leu Leu<br>                 1540                   1545                   1550 | 4654 |
| CCT CCA CCA ATG AGT GCA ATA GAA CCG AAA GTC CCT TAC ACA CCA CTT<br>Pro Pro Pro Met Ser Ala Ile Glu Pro Lys Val Pro Tyr Thr Pro Leu<br>                 1555                   1560                   1565 | 4702 |
| TTG TCT CAG CCA GGG CCC ACT CTT CCT AAG ACC CAT GTG AAA ACA GCC<br>Leu Ser Gln Pro Gly Pro Thr Leu Pro Lys Thr His Val Lys Thr Ala<br>           1570                   1575                   1580 | 4750 |

Figure 4H

```
TCC CTT GGG TTG GCT GGA AAA GCA AGA TCC CCT TTG CTT CCT GTG TCT        4798
Ser Leu Gly Leu Ala Gly Lys Ala Arg Ser Pro Leu Leu Pro Val Ser
    1585            1590                1595

GTG CCA ACA GCC CCT GAA GTG TCT GAG GAG AGC CAC AAA CCA ACA GAG        4846
Val Pro Thr Ala Pro Glu Val Ser Glu Glu Ser His Lys Pro Thr Glu
1600            1605                1610                1615

GAT TCA GCC AAT GTG TAT GAA CAG GAT GAT CTG AGT GAA CAA ATG GCA        4894
Asp Ser Ala Asn Val Tyr Glu Gln Asp Asp Leu Ser Glu Gln Met Ala
                1620                1625                1630

AGT TTG GAA GGA CTC ATG AAG CAG CTT AAT GCC ATC ACA GGC TCA GCC        4942
Ser Leu Glu Gly Leu Met Lys Gln Leu Asn Ala Ile Thr Gly Ser Ala
            1635                1640                1645

TTT TAA CAT GTA TTT CTG AAT GGA TGA GGT GAA TTT TCC GGG AAC TTT        4990
Phe  *  His Val Phe Leu Asn Gly  *  Gly Glu Phe Ser Gly Asn Phe
        1650                1655                1660

GCA GCA TAC CAA TTA CCC ATA AAC AGC ACA CCT GTG TCC AAG AAC TCT        5038
Ala Ala Tyr Gln Leu Pro Ile Asn Ser Thr Pro Val Ser Lys Asn Ser
        1665                1670                1675

AAC CAG TGT ACA GGT CAC CCA TCA GGA CCA CTC AGT TAA GGA AGA TCC        5086
Asn Gln Cys Thr Gly His Pro Ser Gly Pro Leu Ser  *  Gly Arg Ser
1680                1685                1690                1695

TGA AGC AGT TCA GAA GGA ATA AGC ATT CCT TCT TTC ACA GGC ATC AGG        5134
 *  Ser Ser Ser Glu Gly Ile Ser Ile Pro Ser Phe Thr Gly Ile Arg
                1700                1705                1710

AAT TGT CAA ATG ATG ATT ATG AGT TCC CTA AAC AAA AGC AAA GAT GCA        5182
Asn Cys Gln Met Met Ile Met Ser Ser Leu Asn Lys Ser Lys Asp Ala
            1715                1720                1725

TTT T                                                                   5186
Phe
```

FIG. 6

```
        150                                    XbaI                           200
        GATGACATTTTCCCTCTAGAAATTGTGTCTGTACAATGTGTGTATGTGTATATA
        TGTGTGTATGTGTGTGTTTGTGATATATATATATATATAAATCTCCAATGAGATAAGT
                                        300
                              TATATATATATATATATATATATATATATATATATATATATGTCCA
                                                                    250
                                          EcoO109
        CATCATGAATAATAGGGCCCTCTGCTTTCAAGGCAATAACCACTAAA
                                                     350
```

```
                425
DCC      P S S S V L P S A P R D V V P V L V S S - R F V R L S W R P P A E A K G → FIG. 7E
N-CAM(c) P S S - - - P S I D R - V E P - Y S S S T A R V E F D - E P E A T G G
N-CAM(m) P S S - - - P S I D R - V E P - Y S S T A Q V Q F D - E P E A T G G 500                                           525
DCC      E A M Y T F R V V A Y N E W G P G E S S Q P I K V A T Q P - E L Q V P
N-CAM(c) E T T Y S V R L S A V N G K G V G E I S L P S D F K T Q P V R E P S A P
N-CAM(m) E T T Y S D R L A A L N G K G L G E I M Q P S E S K T Q P V P E L S A P 575                                      600
DCC      G - K - E Q N I E V - D G L S - Y K L E G L K K F T E Y S L R F L A Y N → FIG. 7E
N-CAM(c) E W K P E H - - - I R L P S G I D H V M L K S L D W N A E Y E V Y V I A E N
N-CAM(m) E W K P E H - - - I R L P S G S H H V M L K S L D W N A E Y E V Y V V A E N
```

FIG. 7E

```
                475
                 |
N - IQ TFTVFFS - EGD - NRE - RA L NTTQPGSLQ - - LTV - GN LKP
VP HL KYKAEW  - R  AL GEGEWHS R - LYDAKEANVEGT I  SG - LKP
VP IL KYKAEW  - KSL GEESWHFT - WYDAKEANMEGI V  TIMG - LKP

550
                 |
GPVENLQ AVSTSPTS I LITWEPPAYANG - PVQGYR L KFCTEVST
- KLEG - Q - MGEDGNS I KVNVIKQDDG - GSPIRHY - LIYKAKHSS
- KLEG - Q - MGEDGNS I KVNLIKQDDG - GSPIRHY - LVKYRALAS

DCC ANTIBODIES

This application is a Division of U.S. Ser. No. 08/227,527 filed Apr. 14, 1994, now U.S. Pat. No. 5,532,108 which is a continuation of Ser. No. 07/460,981 filed Jan. 4, 1990, now abandoned.

The U.S. Government has a paid-up license in this invention and the right in limited circumstances to require the patent owner to license others on reasonable terms as provided for by the terms of grant numbers GM07309, GM07184, CA09243, and CA35494, awarded by the National Institutes of Health.

TECHNICAL AREA OF THE INVENTION

The invention relates to the area of cancer diagnostics. More particularly, the invention relates to detection of the loss and/or alteration of wild-type DCC genes in tumor tissues.

BACKGROUND OF THE INVENTION

Recent studies have elucidated several genetic alterations that occur during the development of colorectal tumors, the most common of which are deletions of the short arm of chromosome 17 (17p) and the long arm of chromosome 18 (18q). Vogelstein, et al., Science, vol. 244, p. 207 (1989); Fearon, et al., Science, vol. 238, p. 193 (1987); Muleris, et al., Ann. Genet. (Paris), vol. 28, p. 206 (1985); Monpezat, et al., Int. J. Cancer, vol. 41, p. 404 (1988). While some genetic alterations such as RAS gene mutations appear to occur relatively early during colorectal tumor development, chromosome 18q deletions are often late events associated with the transition from Class II to Class III adenomas or the transition from the benign (adenomatous) to the malignant (carcinomatous) state, (Vogelstein et al., New England Journal of Medicine, Vol. 319, p. 525, 1988) and appear to be related to metastasis-and decreased survival time (Kern, et al., JAMA, vol. 261, pp. 13099–13103, 1989). Because carcinomas are often lethal, while the precursor adenomas are uniformly curable, the delineation of the molecular events mediating this transition are of considerable importance.

Allelic deletions have been reported to encompass a large area of chromosome 18q. (Vogelstein, et al., ibid.) This area is known to contain the BCL-2 gene (Tsujimoto, et al., Science, vol. 226, p. 1097 (1984); and Cleary, et al., Cell, vol. 47, p. 19 (1986),) the gastrin-releasing peptide gene (Spindel, et al., Proc. Natl. Acad. Sci., USA, vol. 81, p. 5699 (1984),) and the cellular homologue of the YES-1 oncogene (Semba, et al., Science, vol. 227, p. 1038 (1985) and Yoshida, et al., Cytogenet. Cell Genet., vol. 40, p. 786 (1985)). All of these genes are known to be associated with cancers. If a particular region of the chromosome is the target of the deletions, i.e., it is involved in the neoplastic process, precise delineation of the region is necessary to provide methods of diagnosis as well as therapy.

According to the model of Knudson for tumorigenesis (Cancer Research, vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB and p53, were found to be deleted or altered in many cases of the tumors studied. There is a need in the art of cancer diagnosis and therapy to find other suppressor genes involved in tumorigenesis, so that defects in the suppressor genes or effected cells can be detected and the defects cured to abate or reverse the neoplastic processes.

SUMMARY OF THE INVENTION

It is an object of the present invention to provide a method for diagnosing and prognosing a neoplastic tissue of a human.

It is another object of the invention to provide a method of supplying wild-type DCC gene function to a cell which has lost said gene function.

It is yet another object of the invention to provide a kit for determination of the nucleotide sequence of the DCC gene by the polymerase chain reaction.

It is still another object of the invention to provide nucleic acid probes for detection of mutations in the human DCC gene.

It is another object of the invention to provide a method of detecting genetic predisposition to cancer.

It is still another object of the invention to provide a cDNA molecule encoding the DCC gene product.

It is yet another object of the invention to provide a preparation of the human DCC protein.

These and other objects of the invention are provided by one or more of the embodiments which are described below. In one embodiment of the present invention a method of diagnosing or prognosing a neoplastic tissue of a human is provided comprising: isolating a tissue from a human; and detecting loss of wild-type DCC genes or their expression products from said tissue, said loss indicating neoplasia of the tissue and correlating with metastasis and early death.

In another embodiment of the present invention a method is provided for supplying wild-type DCC gene function to a cell which has lost said gene function by virtue of a mutation in the DCC gene, comprising: introducing a wild-type DCC gene into a cell which has lost said gene function such that said wild-type gene is expressed in the cell.

In another embodiment a method of supplying wild-type DCC gene function to a cell is provided comprising introducing a portion of a wild-type DCC gene into a cell which has lost said gene function such that said portion is expressed in the cell, said portion encoding a part of the DCC protein which is required for non-neoplastic growth of said cell.

In yet another embodiment a kit is provided for determination of the nucleotide sequence of the DCC gene by polymerase chain reaction. The kit comprises: a set of pairs of single stranded DNA primers, the sequence of said set derived from chromosome 18q, said set allowing synthesis of all nucleotides of the DCC gene coding sequences.

In still another embodiment of the invention a nucleic acid probe is provided which is complementary to human wild-type DCC gene coding sequences and which can form mismatches with mutant DCC genes, thereby allowing their detection by enzymatic or chemical cleavage or by shifts in electrophoretic mobility.

In another embodiment a particular nucleic acid probe is provided which hybridizes to a DCC intron which is subject to insertional mutations in tumor cells.

In still another embodiment of the invention a method are provided for detecting the presence of a neoplastic tissue in a human. The methods comprise isolating a body sample from a human; detecting in said sample loss of a wild-type DCC gene sequence or wild-type DCC expression product, said loss indicating the presence of a neoplastic tissue in the human.

In yet another embodiment a method is provided of detecting genetic predisposition to cancer in a human, comprising: isolating a human sample selected from the group consisting of blood and fetal tissue; detecting loss of wild-type DCC gene coding sequences or their expression products from the sample, said loss indicating predisposition to cancer.

In still other embodiments a cDNA molecule is provided which comprises the coding sequence of the DCC gene.

In even another embodiment a preparation of the human DCC protein is provided which is substantially free of other human proteins. The amino acid sequence of the protein is shown in FIG. 5.

The present invention provides the art with the information that the DCC gene, a heretofore unknown gene is, in fact, the target of deletional, insertional, and point mutational alterations on chromosome 18q and that these alterations are associated with the process of tumorigenesis. This information allows highly specific assays to be performed to assess the neoplastic status of a particular tissue or the potential neoplastic status of an individual.

BRIEF DESCRIPTION OF THE DRAWINGS

FIG. 2 shows autoradiographs of Southern blots of DNA from mouse (M), rat (R), hamster (H), chicken (C), Xenopus laevis (F), and S. cerevisiae (Y) hybridized to human fragment O (in the panel on the left) and human fragment P (in the panel on the right). The sizes of the corresponding molecular weight markers in kilobases are indicated between the two panels.

FIG. 3 shows the nucleotide sequence, predicted amino acid (AA) sequence (in single letter code) and splice acceptor and donor features of some human fragments and their corresponding rat homologues. Nucleotide sequences of the rat fragments were identical to those of the human except where indicated. When the predicted amino acid sequence of the rat differed from that of the human, the human sequence is given on the left of the slash and the rat sequence on the right. The regions in human fragment O and P where no corresponding sequence was available for the rat are indicated by the dashed lines. The predicted intron-exon boundaries are indicated by solid arrowheads, and the potential lariat signal preceding the splice acceptor sequence is overlined.

FIG. 4 shows the nucleotide sequence derived from overlapping cDNA clones, prepared from mRNA of either the H82 cell line or from normal human brain. The methionine codon initiating the open reading frame (ORF) is designated as amino acid 202 and the last amino acid is numbered 1648.

FIG. 6 shows the sequence of the 170 bp XbaI-Eco0109 fragment to which the insertions shown in panel A were localized. The numbers above the sequence indicate the distance in bp from the 3' end of the exon contained in fragment P. The XbaI and Eco0109 restriction sites are indicated. The two regions of TA repeats are overlined, and the 130 bp region of alternating purine-pyrimidine sequence is contained between the arrowheads.

FIGS. 7A, 7B, and 7C show a comparison of the sequence homology of the four immunoglobulin-like domains of DCC with one another and with chicken N-CAM [N-CAM(c)] and mouse N-CAM [N-CAM(m)]. The N-CAM(c) and N-CAM(m) sequences shown represent the consensus of the five Ig-like domains present in each protein; if no consensus was present at a particular position of N-CAM(c) or N-CAM (m) (i.e., if no two domains contained the identical residue), then the position is indicated by an X. Spaces inserted for alignment are indicated by a dash. The conserved cysteines thought to be involved in intra-domain disulfide pairing are indicated by solid triangles; other amino acid residues highly conserved in N-CAM and other similar Ig-like domains of the C2 class (Williams, et al., Ann. Rev. Immunol., vol. 6, p. 381, (1988)) are noted by open triangles. Sequences were aligned by inspection to give the greatest overall match. Residues in two or more of the DCC domains were boxed if they were identical. The N-CAM(c) and N-CAM(m) consensus sequences were boxed if they matched the DCC consensus.

FIGS. 7D and 7E show a comparison of the sequence homology between DCC and chicken and mouse N-CAM in the fibronectin-type III-related regions.

DETAILED DESCRIPTION

Figure 1:
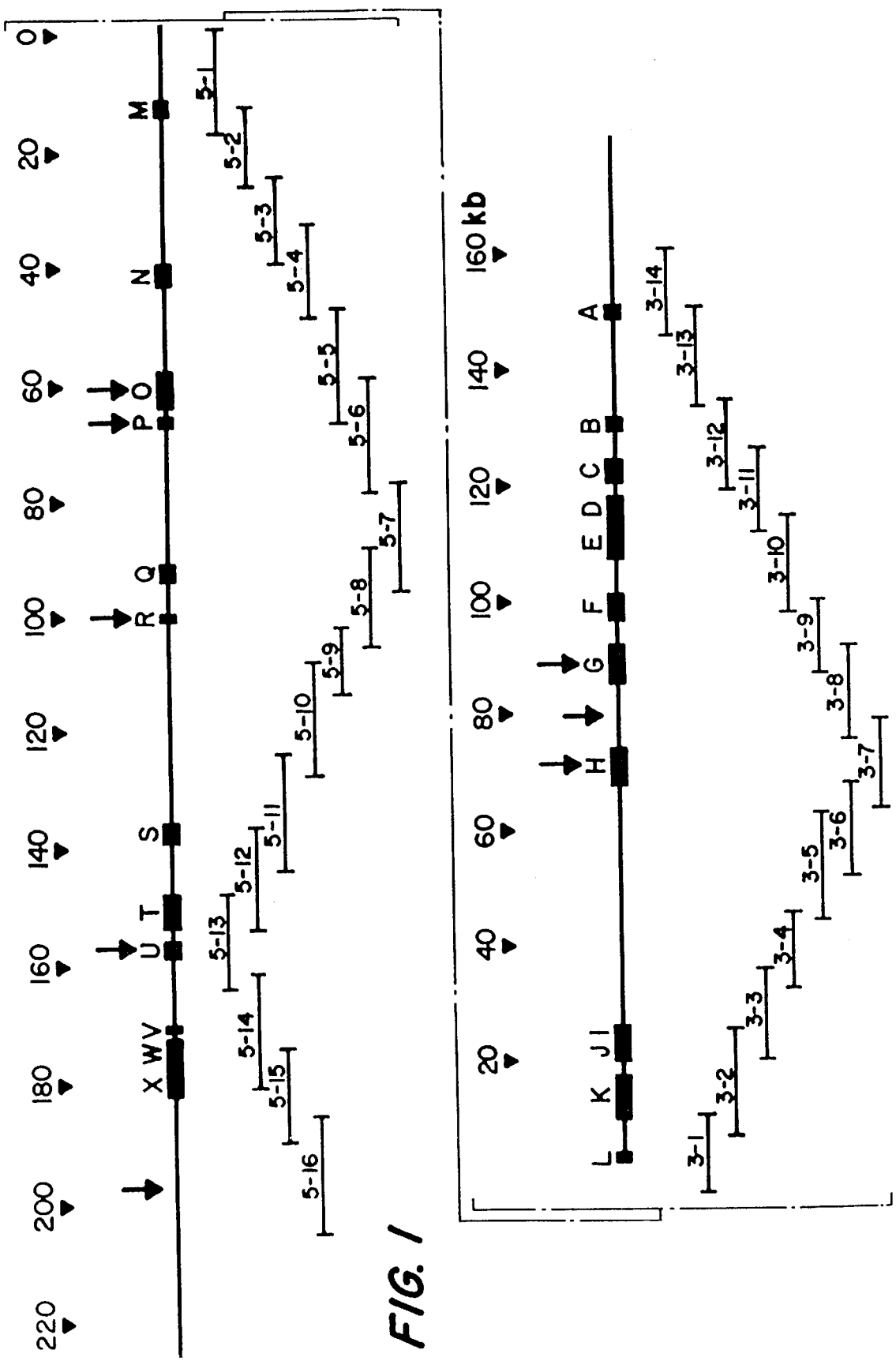
FIG. 1 presents a map of the chromosomal walk and cross-hybridizing fragments in the. DCC region. The DNA region of approximately 370 kb, cloned in 30 rounds of walking, is shown; only the maximal walk for each of the rounds is shown. The map position at "O" marks the location of p15–65. An EcoRI map for the region was constructed and the EcoRI fragments that hybridized at reduced stringency (55° C.) to rodent, chicken, or Xenopus DNA samples are indicated by solid boxes and alphabetical letters (A–X). Human fragments G, I, J, K, M, O, and P were used to isolate rat clones. The minimal region of cross-hybridization was identified and sequenced for both human and rat fragments. The locations of the EcoRI fragments that hybridized to human cDNA clones are indicated by arrows.

It is a discovery of the present invention that mutational events associated with tumorigenesis occur in a previously unknown gene on chromosome 18q named here the DCC (Deleted in Colorectal Carcinomas) gene. Although it was previously known that deletion of alleles on chromosome 18q were common in certain types of cancers, it was not known that the target gene of these deletions was the DCC gene. Further it was not known that other types of mutational events in the DCC gene are also associated with cancers. The mutations of the DCC gene involve gross rearrangements such as insertions and deletions. However point mutations, which lead to loss of expression of wild-type DCC have also been observed.

According to the diagnostic and prognostic method of the present invention, loss of the wild-type gene is detected. The loss may be due to either insertional, deletional or point mutational events. If only a single allele is mutated, an early neoplastic state is indicated. However, if both alleles are mutated then a late neoplastic state is indicated. The finding of DCC mutations thus provides both diagnostic and prognostic information. A DCC allele which is not deleted (e.g., that on the sister chromosome to a chromosome carrying a DCC deletion) can be screened for other mutations, such as insertions, small deletions, and point mutations. It is believed that most mutations found in tumor tissues will be those leading to greatly decreased expression of the DCC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the DCC gene product.

In order to detect the loss of the wild-type DCC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the allele (or alleles) present in the tumor tissue and sequencing that allele(s) using techniques well known in the art. Alternatively, the polymerase chain reaction can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. Insertions and deletions of genes can also be detected by these techniques. In addition, restriction fragment length polymorphism (RFLP) probes for the gene or surrounding marker genes can be used to score loss of an allele or an insertion in a polymorphic fragment. Other techniques for detecting insertions and deletions as are known in the art can be used.

Loss of wild-type genes can also be detected on the basis of the loss of a wild-type expression product of the gene. Such expression products include both the mRNA as well as the protein product itself. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, substitutions or frameshift mutations. Mismatch detection can be used to detect point mutations in the gene or its mRNA product. While these techniques are less sensitive than sequencing, they are simpler to perform on a large number of tumors. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the DCC mRNA or gene but can be a segment of either. If the riboprobe comprises only a segment of the DCC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, vol. 85, 4397, 1988; and Shenk et al., Proc. Natl. Acad. Sci. USA, vol. 72, p. 989, 1975. Alternatively, mismatches can be detected by shifts in the electrophoretic mobility of mismatched duplexes relative to matched duplexes. See, e.g., Cariello, Human Genetics, vol. 42, p. 726, 1988. With either riboprobes or DNA probes, the cellular mRNA or DNA which might contain a mutation can be amplified using PCR (see below) before hybridization. Changes in DNA of the DCC gene can also be detected using Southern hybridization, especially if the changes are gross rearrangements, such as deletions and insertions.

DNA sequences of the DCC gene from the tumor tissue which have been amplified by use of polymerase chain reaction may also be screened using allele-specific probes. These probes are nucleic acid oligomers, each of which contains a region of the DCC gene sequence harboring a known mutation. For example, one oligomer may be about 30 nucleotides in length, corresponding to a portion of the DCC gene sequence. By use of a battery of such allele-specific probes, the PCR amplification products can be screened to identify the presence of a previously identified mutation in the DCC gene. Hybridization of allele-specific probes with amplified DCC sequences can be performed, for example, on a nylon filter. Hybridization to a particular probe under stringent hybridization conditions indicates the presence of the same mutation in the tumor tissue as in the allele-specific probe.

Loss of DCC mRNA expression can be detected by any technique known in the art. These include Northern analysis, PCR amplification and RNase protection. Diminished mRNA expression indicates a loss of the wild-type DCC gene.

Loss of wild-type DCC genes can also be detected by screening for loss of wild-type DCC protein. For example, monoclonal antibodies immunoreactive with DCC can be used to screen a tissue. Lack of antigen would indicate a DCC mutation. Antibodies specific for mutant alleles could also be used to detect mutant DCC gene product. Such immunological assays could be done in any convenient format known in the art. These include Western blots, immunohistochemical assays and ELISA assays. Any means for detecting an altered DCC protein can be used to detect loss of wild-type DCC genes. Finding a mutant DCC gene product indicates loss of a wild-type DCC gene.

Mutant DCC genes or gene products can also be detected in other human body samples, such as, serum, stool, urine and sputum. The same techniques discussed above for detection of mutant DCC genes or gene products in tissues can be applied to other body samples. Cancer cells are sloughed off from tumors and appear in such body samples. In addition, the DCC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant DCC genes or gene products.

The methods of diagnosis of the present invention are applicable to any tumor in which DCC has a role in tumorigenesis. The diagnostic method of the present invention is useful for clinicians so that they can decide upon an appropriate course of treatment. For example, a tumor displaying loss of both DCC alleles might suggest a more aggressive therapeutic regimen than a tumor displaying loss of only one DCC allele.

The primer kit of the present invention is useful for determination of the nucleotide sequence of the DCC gene using the polymerase chain reaction. The kit comprises a set of pairs of single stranded DNA primers which can be annealed to sequences within or surrounding the DCC gene on chromosome 18q in order to prime amplifying DNA synthesis of the DCC gene itself. The complete set allows synthesis of all of the nucleotides of the DCC gene coding sequences, i.e., the exons. The set of primers preferably allows synthesis of both intron and exon sequences, as a number of DCC mutations have been found in a DCC intron. The kit can also contain DNA polymerase, preferably Taq polymerase, and suitable reaction buffers. Such components are known in the art.

In order to facilitate subsequent cloning of amplified sequences, primers may have restriction enzyme sites appended to their 5' ends. Thus, all nucleotides of the primers are derived from DCC sequences or sequences adjacent to DCC except the few nucleotides necessary to form a restriction enzyme site. Such enzymes and sites are well known in the art. The primers themselves can be synthesized using techniques which are well known in the art. Generally, the primers can be made using synthesizing machines which are commercially available. Given the sequence of the DCC open reading frame shown in FIG. 4, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the DCC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, vol. 83, p. 586, 1986. Generally, the probes are complementary to DCC gene coding sequences, although probes to certain introns are also contemplated. One probe in particular hybridizes to the XbaI-Eco0109 fragment located 165 bp downstream from the DCC exon in fragment P shown in FIG. 3. Another probe hybridizes to fragment P itself, and is a probe for DCC coding sequences. An entire battery of nucleic acid probes is used to compose a kit for detecting loss of wild-type DCC genes. The kit allows for hybridization to the entire DCC gene. The probes may overlap with each other or be contiguous.

If a riboprobe is used to detect mismatches with mRNA, it is complementary to the mRNA of the human wild-type DCC gene. The riboprobe thus is an anti-sense probe in that it does not code for the DCC protein because it is of the opposite polarity to the sense strand. The riboprobe generally will be radioactively labeled which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of DCC gene. These are useful to detect similar mutations in other patients on the basis of hybridization rather than mismatches. These are discussed above and referred to as allele-specific probes. As mentioned above, the DCC probes can also be used in Southern hybridizations to genomic DNA to detect gross chromosomal changes such as deletions and insertions. The probes can also be used to select cDNA clones of DCC genes from tumor and normal tissues. In addition, the probes can be used to detect DCC mRNA in tissues to determine if expression is diminished as a result of loss of wild-type DCC genes. Provided with the DCC coding sequence shown in FIG. 4, design of particular probes is well within the skill of the ordinary artisan.

According to the present invention a method is also provided of supplying wild-type DCC function to a cell which carries mutant DCC alleles. The wild-type DCC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant DCC allele, the gene portion should encode a part of the DCC protein which is required for non-neoplastic growth of the cell. More preferred is the situation where the wild-type DCC gene or a part of it is introduced into the mutant cell in such a way that it recombines with the endogenous mutant DCC gene present in the cell. Such recombination requires a double recombination event which results in the correction of the DCC gene mutation. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type DCC-gene can be used as model systems to study cancer remission and drug treatments which promote such remission.

Polypeptides which have DCC activity can be supplied to cells which carry mutant or missing DCC alleles. The sequence of the DCC protein is disclosed in FIG. 4. Protein can be produced by expression of the cDNA sequence in bacteria, for example, using known expression vectors. Alternatively, DCC can be extracted from DCC-producing mammalian cells such as brain cells. In addition, the techniques of synthetic chemistry can be employed to synthesize DCC protein. Any of such techniques can provide the preparation of the present invention which comprises the DCC gene product having the sequence shown in FIG. 4. The preparation is substantially free of other human proteins. This is most readily accomplished by synthesis in a microorganism or in vitro. Active DCC molecules can be introduced into cells by microinjection or by use of liposomes, for example. Alternatively, some such active molecules may be taken up by cells, actively or by diffusion. Extracellular application of DCC gene product may be sufficient to effect tumor growth, as DCC may act at the cell surface like its homologues, the neural cell adhesion molecules. Supply of molecules with DCC activity should lead to a partial reversal of the neoplastic state. Other molecules with DCC activity may also be used to effect such a reversal.

The present invention also provides a preparation of antibodies immunoreactive with human DCC protein. The antibodies may be polyclonal or monoclonal and may be raised against native DCC protein or DCC fusion proteins. The antibodies should be immunoreactive with DCC epitopes, preferably epitopes not present on other human proteins. In a preferred embodiment of the invention the antibodies will immunoprecipitate DCC proteins from solution as well as react with DCC protein on Western blots of polyacrylamide gels. Techniques for raising and purifying antibodies are well known in the art and any such techniques may be chosen to achieve the preparation of the invention.

Predisposition to cancers can be ascertained by testing normal tissues of humans for mutations of DCC gene. For example, a person who has inherited a germline DCC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells or amniotic fluid for mutations of the DCC gene. Loss of a wild-type DCC allele, whether for example, by point mutation or by deletion, can be detected by any of the means discussed above.

Molecules of cDNA according to the present invention are intron-free, DCC gene coding molecules. They can be made by reverse transcriptase using the DCC mRNA as a template. These molecules can be propagated in vectors and cell lines as is known in the art. Such molecules have the sequence shown in FIG. 4. The cDNA can also be made using the techniques of synthetic chemistry given the sequence disclosed herein.

The following are provided for exemplification purposes only and are not intended to limit the scope of the invention which has been described in broad terms above.

Example 1

This example demonstrates that the locus on chromosome 18q which is the subject of frequent allelic deletions and of somatic mutations is expressed in cell lines of lung and colorectal carcinoma.

Tumor S123 was found to have a different hybridization pattern from normal colonic mucosa of the same patient when probed with probe p15–65. The tumor displayed a heterozygous pattern with two MspI alleles of 7.8 and 10.5 kb. The normal colonic mucosa was homozygous for the 7.8 kb allele.

The p15–65 probe contains a 2.7 kb SalI-EcoRI fragment derived from sequences adjacent to and including those contained within the anonymous DNA segment OLVII E10. Marlhens, et al., Nucl. Acids. Res., vol. 15, p. 1348, 1987. OLVII E10 is an 0.8 kb Hind III-EcoRI fragment that marks the D18S8 locus at 18q21.3 and detects MspI polymorphisms in normal individuals. Plasmid p15–65 was derived from a human genomic DNA library prepared from human DNA partially digested with MboI and cloned in lambda FIX (Stratagene). Two phage clones hybridizing to OLVII E10 were isolated by hybridization selection. Among several tested subfragments from the two phage clones identified, p15–65 produced the highest signal to noise ratio when used for Southern blot experiments. Plasmid p15–65 (and OLVII E10) detect polymorphic MspI sites, and thus give rise to four alleles of 10.5, 9.7, 7.8, and 7.0 kb at frequencies of 17%, 4%, 49% and 30%, respectively (N=232).

In order to determine the molecular basis of the acquisition of heterozygosity in the carcinoma tissue of patient S123, genomic DNA clones containing the effected MspI site were isolated from the carcinoma and compared to normal DNA sequences. Except for MspI, the restriction maps to this region were identical in the tumor and normal tissue of patient S123 indicating no gross DNA additions or deletions in the tumor. The affected MspI site was found to lie within an Alu-type repeated element in a 1.8 kb EcoRI fragment which is 5 kb from p15–65. The sequence of the cloned DNA fragment from the S123 tumor DNA differed from the normal allele at a single base pair, resulting in the replacement of the internal G residue within the MspI recognition sequence 5'-CCGG-3' with an A residue. This mutation created a potential 3' splice acceptor site, identical to the consensus sequence for intron-exon junctions of primate genes (Shapiro, et al., Nucleic Acids Res., vol. 15, p. 7155, 1987; Ruskin, et al., Cell, vol. 38, p. 317, 1984; and Zhuang, et al., Proc. Natl. Acad. Sci. USA, vol. 86, p. 2752, 1989.) It is noted that mutations creating splice acceptor sites associated with abnormal RNA processing have been previously found in inherited diseases, such as thalassemias (Ley, et al., Proc. Natl. Acad. Sci., USA, vol. 79, p. 4775, 1982; and Sharp, Annual Reviews of Biochem., vol. 55, p. 1119, 1986.)

Phage clones that encompassed a 35 kb region surrounding the mutated MspI site of tumor S123 were isolated. All EcoRI fragments from the phage clones were subcloned and used in hybridization experiments with Northern blots containing RNA of normal colonic mucosa and cell lines derived from tumors of the colon and several other organs. No expression was detected in these experiments, nor was expression detected in RNase protection studies of these RNA samples using selected subfragments from the phage clones. A more exhaustive strategy was therefore undertaken to identify expressed from this region of chromosome 18q.

A bidirectional chromosomal walk from this region was carried out using bacteriophage vectors. Over 140 unique clones, spanning approximately 370 kb, were isolated in 30 rounds of walking; the clones representing the maximal walk for each of the 30 rounds are shown in FIG. 1. The clones were obtained as follows.

Human genomic DNA was partially-digested with MboI and fragments of 12–18 kb were cloned in the lambda FIX vector (Stratagene) using conditions recommended by the manufacturer. Clones were propagated in E. coli C600 or TAP 90 cells (Patterson, et al., Nucleic Acids Res., vol. 15, p. 6298, 1987). For each round of walking, EcoRI maps were constructed from comparison of digests of overlapping phage clones (starting with page clones containing p15–65). EcoRI fragments mapping furthest from previously obtained phage clones were used to re-screen the library. Approximately $1 \times 10^6$ phage clones were screened for each round of walking; three to seven new clones were generally obtained in each walk, and the clones purified through three rounds of hybridization selection.

In an effort to identify potential exons in the 370 kb region on the basis of their homology to other species, every EcoRI fragment from the region was isolated and used as a hybridization probe at reduced stringency (conditions as described in Vogelstein, et al., Cancer Res., vol. 47, p. 4806, 1987 except that the hybridization buffer contained 0.5% non-fat dried milk and filter washing was performed in 44.5 mM sodium chloride, 1.8 mM sodium citrate, 0.3 mM Tris, pH7.5 at 55° C. for 45 minutes) to screen DNA samples from various species (mouse, rat, hamster, chicken, Xenopus and yeast). Such a strategy for the identification of exons was employed for the Duchenne muscular dystrophy gene and cystic fibrosis genes. (Monaco, et al., Nature, vol. 323, p. 646, 1986 and Rommens, et al., Science, vol. 245, p. 1059, 1989). Twenty-four of the 117 EcoRI fragments hybridized to discrete DNA fragments of at least one of the species tested; these fragments are indicated by the solid boxes in FIG. 1. The patterns observed with two of the fragments producing strong cross-species hybridization are illustrated in FIG. 2. Fragment O hybridized strongly to mouse, rat, hamster, and Xenopus DNAS, and fragment P hybridized strongly to mouse, rat, and hamster DNAs.

Most of the cross-species hybridizing fragments were then used as probes to screen Northern blots prepared with RNA of various normal tissues or tumor cell lines, and also used to screen cDNA libraries from normal colonic mucosa specimens, a colorectal adenoma cell line, a brain tumor, a fibrosarcoma line, and an embryonal carcinoma line. No evidence for expression was obtained in these Northern blot studies, nor were any hybridizing clones identified in any of the cDNA libraries using the cross-hybridizing fragments as probes.

In order to determine if any of the cross-hybridizing fragments had exon-like structural features, we cloned several of the homologous fragments from the rat, and determined the regions of cross-hybridization for each fragment for both human and rat.

Rat genomic clones were obtained in two ways. In some cases, fragments identified on Southern blots by cross-species hybridization were eluted from agarose gels and cloned (as described for the human genomic clones above) using cross-hybridizing, radiolabeled human clones as probes. In other cases, MboI partial digests of rat genomic DNA were cloned in lambda DASH (Stratagene) using conditions recommended by the manufacturer, and the library was screened with homologous human clones of interest.

The cross-hybridizing regions were then subcloned and sequenced from both species; the seven regions for which this analysis was performed are G, I, J, K, M, O and P. The sizes of the regions of homology studied ranged from 128 to over 534 bp, and their homology ranged from 75–89%. The sequences were examined for open reading frames (ORFs), conservation in the predicted amino acid sequence of the ORFs, consensus mammalian splice acceptor and lariat sequences at the 5' end of the ORFS, and consensus splice donor sequences at the 3' region of the ORFs (Shapiro, et al., Nucleic Acids Res., vol. 15, p. 7155, 1987; and Ruskin et al., Cell, vol. 38, p. 317, 1984). Several of these features were found in most of the fragments sequenced. Three of the human-rat fragment pairs (fragments G, O, and P in FIGS. 1 and 3) were found to have more exon-like features than the other fragments. The region of cross-species hybridization from human fragment G and its homologous rat fragment predicted ORFs that differed at two amino acid positions (FIG. 3). Similarly, the ORFs predicted for the other two sets of fragments were highly conserved with a single amino acid substitution distinguishing human fragments O and P from their respective rat homologues (FIG. 3). For all three sets of fragments, nucleotide substitutions were predominantly at the third position of codons in the exon-like regions, and sequence homology decreased to 75% or less outside these regions.

The striking homology between the human and rat sequences and their exon-like structural features suggested that the fragments might contain potential exons. However, as noted above, no expression was detected when these three fragments were used as probes of Northern blots of various RNAs or used to screen cDNA libraries. In addition, RNase protection experiments (Winter, Proc. Natl. Acad. Sci. USA, vol. 82, p. 7575, 1985), using these three fragments to generate anti-sense transcripts, failed to conclusively demonstrate evidence of expression in a variety of RNA samples, including normal colonic mucosa, colorectal cell lines, and other tumor cell lines of various types.

To increase the sensitivity of expression assays, we utilized the polymerase chain reaction (PCR, Saiki, et al., Science, vol. 239, p. 487, 1988) in an "exon-connection" strategy. cDNA was prepared from total RNA of various cell lines and tissues using reverse transcriptase to prime synthesis with random hexamers (Noonan, et al., Nucleic Acids Res., vol. 16, p. 10366, 1988). This single-stranded cDNA was then used in PCR experiments with oligonucleotide pairs derived from the sequence of two of the potential exons noted above. If the two potential exons were present in the same RNA transcript, then, using the appropriate oligonucleotides, it would be possible to amplify a cDNA product linking these two regions. Trace amounts of DNA, which often contaminate RNA preparations, would not give rise to the same sized PCR product in this assay because the exons were separated by an intron. Most pairs of oligonucleotides derived from the seven regions of human-rat homology described above did not generate discrete PCR fragments when tested by this strategy. However, an oligonucleotide pair derived from the sequence of fragments O and P of FIG. 3 was found to generate a discrete 233 bp PCR product from cDNA of several of the mRNA samples studies, including that derived from a small cell carcinoma of the lung (H82) and a colorectal carcinoma (HCT116).

The oligonucleotide derived from fragment O was 5'-TTCCGCCATGGTTTTTAAATCA-3' and the oligonucleotide derived from fragment P was 5'-AGCCTCATTTTCAGCCACACA-3'. Cycle times were 1 minute at 95° C., 1 minute at 58° C., and 2 minutes at 70° C.; twenty-five cycles were performed. The PCR products were phosphorylated using T4 DNA kinase (Bethesda Research Laboratories), ligated to EcoRI linkers (New England Biolabs), inserted into lambda gt10 phage arms (Stratagene), and cloned in E. coli C600 cells. Insert-containing clones were identified through hybridization with radiolabeled probes from fragments O and P (FIG. 3). EcoRI inserts from the phage clones were subcloned in Bluescript SK (Stratagene) and sequenced as described by S. Tabor and C. C. Richardson, Proc. Natl. Acad. Sci. USA, vol. 84, p. 4767, 1987; and Kraft, et al., Biotech., vol. 6, p. 544, 1988. The PCR products from both cell lines 482 and HCT 116 were found to be the product of splicing the predicted exon of fragment O directly to the predicted exon of fragment P. Thus the region of chromosome 18q is expressed.

Example 2

This example demonstrates the isolation and sequencing of the cDNA corresponding to the coding sequence of the gene which is deleted in colorectal carcinomas.

To confirm and extend these PCR experiments, we constructed a cDNA library from RNA of the H82 cell line (Gubler, et al., Gene, vol. 25, p. 263, 1983). Approximately $3.0 \times 10^6$ recombinant cDNA clones were screened with genomic DNA subclones containing regions of fragments G, O, and P of FIG. 3. Four hybridizing clones were isolated and mapped with respect to one another and to the genomic clones shown in FIG. 1. The longest clone was 1.65 kb in length and hybridized to at least eleven unique EcoRI fragments in human genomic DNA, eight of which were present within the 370 kb region cloned in the chromosomal walk shown in FIG. 1. The four cDNA clones isolated were sequenced and subsequently used as probes of cDNA libraries obtained from H82 cells or from normal human brain to obtain additional cDNA clones extending for a total of 2854 base pairs. Through sequencing, all clones were found to encode overlapping portions of a transcript in which there was a single long ORF of 2250 bp, which extended to the end of the sequenced region. The ORF began with a methionine codon in a favorable context for translation initiation (nucleotide 605 in FIG. 4) according to the paradigms of Kozak, Nucl. Acids Res., vol. 15, p. 8125, 1987. The methionine was followed by a relatively hydrophobic sequence of 25 amino acids which resembled previously described signal sequences associated with membrane-bound proteins (Watson, Nucleic Acids Res., vol. 12, p. 5145, 1984). The signal sequence was immediately followed by 725 amino acids with significant homology to the neural cell adhesion molecules and other related cell surface glycoproteins. The gene encoding this transcript will be referred to as DCC (Deleted in Colorectal Carcinomas).

Example 3

This example demonstrates that most normal tissues of rat and human produce the DCC transcript. However most colorectal tumor cell lines do not produce amounts as great as are produced in normal cells.

To identify the tissues in which the DCC gene was expressed, cDNA was prepared from several rat organs. These were: liver, kidney, adrenal, heart, lung, stomach, esophagus, spleen, small bowel, breast, bladder, uterus, aorta, psoas, brain, colon, tongue and skin. Because of the high degree of conservation of the DCC gene (see FIG. 3), the same oligonucleotide primers used to demonstrate expression in human cells could also be used in the rat. To assess expression, oligonucleotide pairs from fragments 0 and P of FIG. 3 were used in a PCR expression assay as described above.

Figure 5:
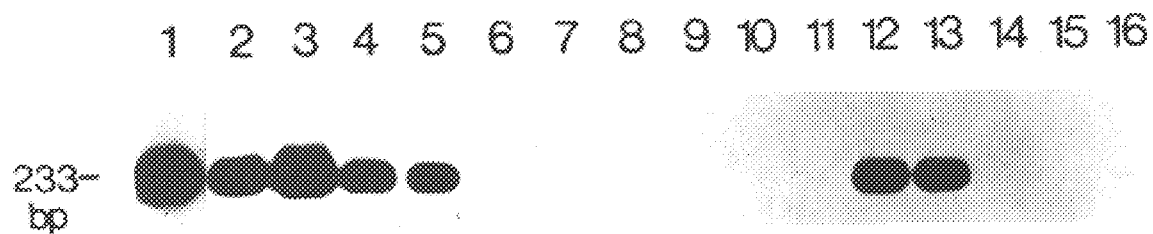
FIG. 5 demonstrates expression of DCC in human tumors and colorectal tumor cell lines. RNA was isolated and used as template to prepare a first strand of cDNA. The cDNA samples were used for polymerase chain reaction (PCR) analysis. The PCR products were separated by electrophoresis through an agarose gel, and after Southern transfer, hybridized to a radioactively-labeled subclone of fragment P. RNA was isolated from normal human brain (lane 1), four different normal colonic mucosa specimens (lanes 2–5) or colorectal carcinoma cell lines (lane 6–16).

Seventeen of the eighteen rat tissues tested appeared to produce the transcript at low levels, with greatest abundance observed in brain (Chomezynski, et al., Anal. Biochem., vol. 162, p. 156, 1987). Only the liver did not produce detectable transcript. Similar analysis of human tissues and cell lines revealed that the transcript was present in highest concentration in brain, and was also expressed in normal colonic mucosa and in several tumor cell lines, including those derived from tumors of the lung, brain and mesenchyme (FIG. 5 and data not shown). In most colorectal carcinomas, however, expression was greatly reduced or absent; of seventeen colorectal tumor cell lines studied, only two expressed DCC mRNA at levels in excess of 5% of that produced in normal colonic mucosa (examples in FIG. 5). The human colorectal carcinoma cell lines used were: lane 6, SW948; lane 7, SW1417; lane 8, SW1116; lane 9, SW403; lane 10, SW1463; lane 11, SW48; lane 12, HCT116; lane 13, RKO; lane 14, RCA; lane 15, "C"; lane 16, MOSER.

To determine the size of the transcript produced from this gene, Northern blots containing RNA from normal colonic mucosa or brain were hybridized with radioactively labelled cDNA clones. A major band of 10–12 kb was observed in normal brain RNA, but no bands were seen in the RNA from colonic mucosa (data not shown), consistent with the higher level of expression observed in brain by PCR analysis.

Example 4

This example demonstrates that the boundary of the deletion of one of the alleles in the S115 tumor is within the DCC gene and that rearrangements of the gene can be detected in human cells using CDNA probes.

In an attempt to establish the boundaries of the homozygous loss in the S115 tumor with respect to the DCC gene, the cDNA clones were used to probe Southern blots containing S115 DNA. A 430 bp subclone (pKC430, representing nucleotide 1760 to 2205 of the cDNA) detected three EcoRI fragments of 20 kb, 10 kb, and 1.8 kb in DNA from non-neoplastic colonic mucosa of patient S115. However, in DNA from the S115 tumor, the 20 kb fragment was not detected and the 10 kb and 1.8 kb fragments were present at approximately half the intensity observed in normal DNA. In addition, a new fragment of 5 kb was observed only in DNA from the tumor. Probes more 3' than pKC430 also detected fragments in tumor DNA which were present at half the intensity of those seen in normal DNA, while probes 5' of pKC430 detected fragments which were homozygously deleted in the tumor. Thus, the DCC gene appeared to be broken by the deletion event on one of the two copies of chromosome 18, and the breakpoint established one boundary of the homozygous loss.

Example 5

This example demonstrates that the EDNA probes of the present invention can be used to detect genetic alterations in DNA samples isolated from colorectal tumors.

To search for other genetic alterations, the cDNA probes were used in Southern blot analysis of colorectal tumor DNA samples. DNA from normal and tumor DNA samples were digested with EcoRI and Eco0109 and Southern blots were prepared as described above. The DNA was then hybridized to a 0.4 kb genomic fragment which contained the exon from fragment P.

Three of 51 primary tumors and two of twenty-one tumor xenografts were found to have new fragments not present in normal DNA of the same patient. In addition, five of twenty-two colorectal tumor cell lines were found to have altered fragments not present in forty-four DNA samples from normal individuals nor in any of the 45 DNA samples from tumor cell lines derived from tissues other than that of the colon or rectum.

In all cases, detailed mapping experiments showed that the new fragments detected by the cDNA probe resulted from insertions in an approximately 170 kb XbaI-Eco0109 fragment located 165 bp down-stream of the exon in fragment P of FIG. 3. The insertions were mapped by comparison of Southern blot patterns produced by digestion of tumor DNA samples with a combination of XbaI and Eco0109, and HindIII. The size of the insertion in the tumors varied from 120–300 bp. Some variation in the size of the XbaI-Eco0109 fragment in alleles from normal individuals was seen; however, the maximal difference between the size of the smallest and largest of the 88 normal alleles studied was approximately 35 bp, and the largest of the normal alleles was found to be approximately 120 bp smaller than any of the altered alleles seen in the tumors.

The 1.4 kb EcoRI fragment (fragment P) containing the insertion site was isolated from one of the genomic clones of the chromosome walk (FIG. 1) and sequenced; the sequence of the 170 bp XbaI-Eco0109 fragment from this fragment is shown in FIG. 6. There were two regions of TA repeats in the XbaI-Eco0109 fragment; one of the regions had eight repeats and the other had twenty-six. Both TA repeat regions were contained within a 130 bp region of alternating purine-pyrimidine base pairs which could potentially form Z-DNA (Rich, et al., Annu. Rev. Biochem., vol. 53, p. 791, 1984).

Example 6

This example demonstrates the sequence similarity between four immunoglobulin-like domains of the DCC gene with the chicken N-CAM and mouse N-CAM genes.

Figure 7C:
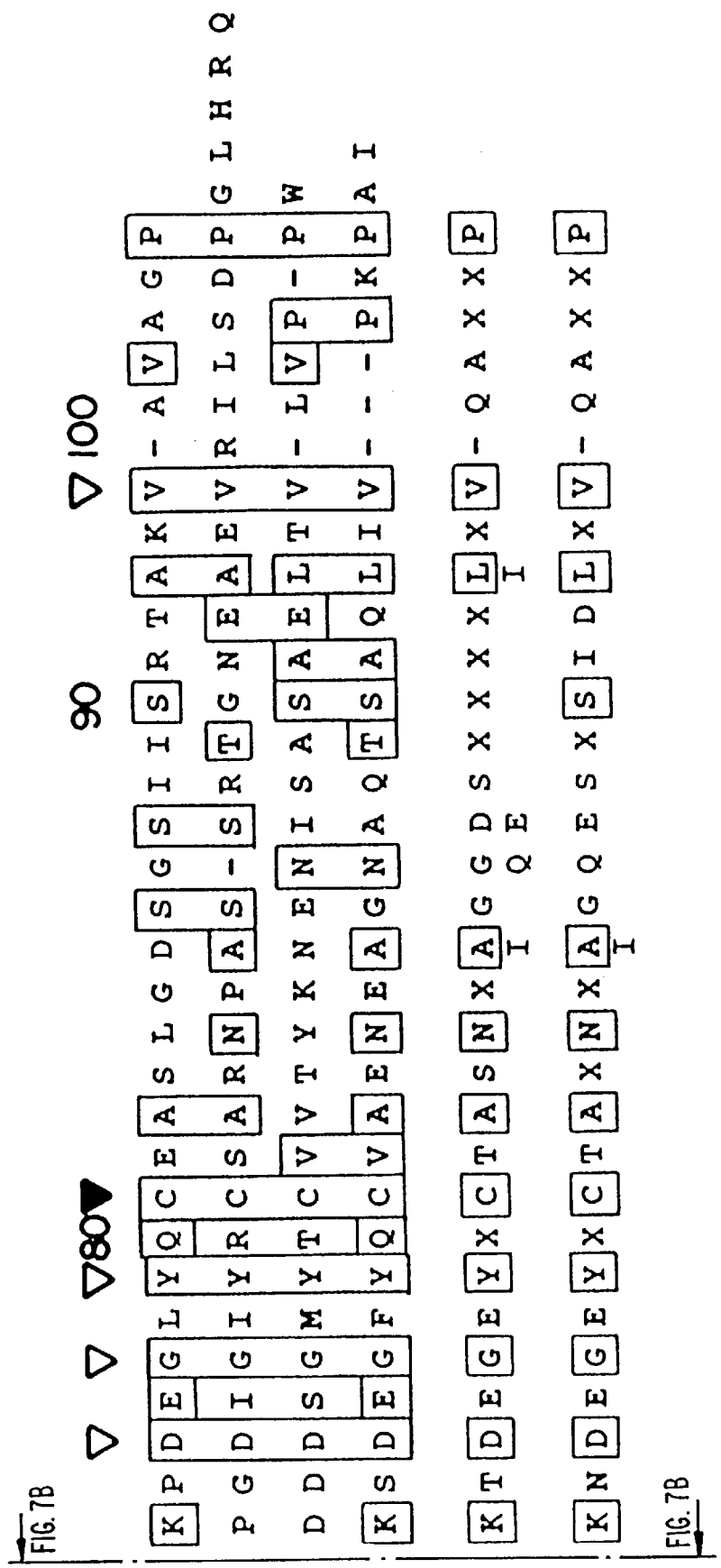

The predicted amino acids sequence of DCC is highly homologous to the neural cell adhesion molecules (N-CAM) and other related cell surface glycoproteins. (Edelman, Biochem., vol. 27, p. 3535, 1988). Two areas of high homology are noted. First the DCC gene contains four immunoglobulin-like (Ig-like) domains of the C2 class, defined by pairs of cysteines separated by 50 to 56 amino acids and other highly conserved residues surrounding the first and second cysteine of each pair. (See FIGS. 7A, 7B, and 7C and Williams, Ann. Rev. Immunol., vol. 6, p. 381, 1988).

Sequences of the domains were aligned by inspection and spaces, indicated by dashes were inserted to give the greatest overall match. Residues in two or more of the DCC domains were boxed if they were identical. Each Ig-like domain is approximately 100 amino acids in length. DCC domain no. 1 includes amino acids 40 to 139 (numbered 241 to 340 in FIG. 4), domain no. 2 includes amino acids 140–239 (numbered 341–440 in FIG. 4), domain no. 3 includes amino acids 240–332 (numbered 441–533 in FIG. 4), and domain no. 4 includes amino acids 333–422 (numbered 534–623 in FIG. 4). The four Ig-like domains of DCC were found to be more homologous to one another than to N-CAM L1, or other members of the Ig super-family. A consensus sequence for the four Ig-like domains of DCC could be derived for 67% of the positions; the DCC consensus sequence matched the N-CAM consensus sequence, at 42% of these positions.

Sequence homology between the DCC and chicken and mouse N-CAM genes was also found in the fibronectin-type III-related regions. DCC amino acid positions 423 to 605 (numbered 624 to 806 in FIG. 4) were compared to amino acids 481 to 662 of the two N-CAM proteins. Potential sites of N-linked glycosylation are found at several positions within this region.

The fibronectin-type III-related domain is similar to the fibronectin-like domains present in N-CAM, L1, leucocyte common antigen related gene 1 (Lar1), fasciclin II, and other members of the cell adhesion molecule family. These fibronectin-related domains are carboxyl to the Ig-like domain in all of these proteins including DCC. Of 195 positions within the fibronectin-like region of DCC, 31% were identical in DCC and N-CAM and several conservative substitutions were also found FIGS. 7D and 7E. The extensive homologies in both Ig-like and fibronectin-like domains between DCC and other members of this family suggest that these proteins may all have been derived from a common precursor that included both these regions.

Example 7

This example demonstrates the expression of the DCC protein in bacteria and the production of anti-DCC antibodies.

The DCC CDNA sequence shown in FIG. 4 was inserted in a bacterial expression vector, pEX2. The vector will produce the protein of any open reading frame as a fusion product with beta-galactosidase. (See Stanley, et al., The EMBO Journal, vol. 3, pp. 1429–1434, 1984.) The bacterially expressed DCC protein was partially purified and injected into rabbits together with Freund's adjuvant. The rabbits were given three monthly booster injections. The rabbits produced antibodies which immunoprecipitate DCC proteins synthesized in in vitro translation reactions. The antibodies also bind to DCC on Western blots.

I claim:

1. A preparation of antibodies which binds to human DCC protein and does not bind to N-CAM proteins.
2. A preparation of antibodies which binds to an epitope of human DCC protein wherein the epitope does not include amino acids 40–605 of human DCC protein.
3. The preparation of claim 1 wherein the antibodies are polyclonal.
4. The preparation of claim 1 wherein the antibodies are monoclonal.
5. The preparation of claim 2 wherein the antibodies are polyclonal.
6. The preparation of clam 2 wherein the antibodies are monoclonal.

* * * * *